(12) United States Patent
Mahurkar (10) Patent No.: US 6,500,129 B1
(45) Date of Patent: Dec. 31, 2002

(54) HYPODERMIC NEEDLE ASSEMBLY

(76) Inventor: Sakharam D. Mahurkar, 6171 N. Sheridan Rd., Suite 1112, Chicago, IL (US) 60660

( * ) Notice: Subject to any disclaimer, the term of this patent is extended or adjusted under 35 U.S.C. 154(b) by 0 days.

(21) Appl. No.: 09/881,630

(22) Filed: Jun. 14, 2001

Related U.S. Application Data

(62) Division of application No. 08/859,140, filed on May 20, 1997, now Pat. No. 6,280,401, which is a continuation-in-part of application No. 08/573,663, filed on Dec. 18, 1995, now Pat. No. 5,685,862, which is a division of application No. 08/229,811, filed on Apr. 19, 1994, now Pat. No. 5,514,100, which is a division of application No. 08/111,372, filed on Aug. 23, 1993, now Pat. No. 5,338,311.

(51) Int. Cl.$^7$ .............................. A61B 5/00; B65D 81/00
(52) U.S. Cl. ...................... 600/576; 128/919; 604/195
(58) Field of Search ............................... 600/573, 576, 600/577, 578; 604/110, 181, 187, 188, 192, 194, 195, 196, 198, 218, 240, 242, 243; 128/919

(56) References Cited

U.S. PATENT DOCUMENTS

| 2,888,923 A | 6/1959 | Reis |
| 2,925,083 A | 12/1960 | Craig |
| 3,610,240 A | 10/1971 | Harautuneian |
| 3,658,061 A | 4/1972 | Hall |
| 4,068,659 A | 1/1978 | Moorehead |
| 4,233,982 A | 11/1980 | Bauer et al. |
| 4,245,635 A | 1/1981 | Kontos |
| 4,261,357 A | 4/1981 | Kontos |
| 4,274,408 A | 6/1981 | Nimrod |
| 4,417,886 A | 11/1983 | Franhouser et al. |
| 4,424,833 A | 1/1984 | Spector et al. |
| 4,425,120 A | 1/1984 | Sampson et al. |
| 4,468,224 A | 8/1984 | Enzmann et al. |
| 4,529,399 A | 7/1985 | Groshong et al. |
| 4,631,057 A | 12/1986 | Mitchell |

(List continued on next page.)

FOREIGN PATENT DOCUMENTS

| DE | 24 15 196 | 10/1975 |
| DE | 25 07 119 | 9/1976 |
| DE | 30 42 229 | 5/1982 |
| DE | 38 33 138 | 4/1990 |
| EP | 0 360 313 | 3/1990 |
| FR | 2004771 | 11/1969 |
| WO | WO 84/01510 | 4/1984 |
| WO | WO90/15634 | 12/1990 |
| WO | WO 93/00950 | 1/1993 |
| WO | WO 97/06841 | 2/1997 |

OTHER PUBLICATIONS

"Health Care" by Helene Cooper, Wall Street Journal (Nov. 25, 1992).

The G.M.P. Letter (May 1992).

(List continued on next page.)

*Primary Examiner*—Kevin Shaver
*Assistant Examiner*—Charles Marmor, II
(74) *Attorney, Agent, or Firm*—Jenkens & Gilchrist (57) ABSTRACT

A hypodermic-needle sample collection device includes an elongated, generally cylindrical barrel forming an aperture at the distal end of the barrel and opening into the interior of the barrel, and a needle holder mounted for longitudinal movement within the barrel. The needle holder includes a pin projecting laterally therefrom. A hollow needle carried by the needle holder projects from the holder along the axis of the barrel. The pin is guided by longitudinal linear and spiral guide surfaces extending along at least a portion of the length of the barrel for moving the needle longitudinally within the barrel in response to relative rotational movement between the linear and spiral guide surfaces.

24 Claims, 11 Drawing Sheets

U.S. PATENT DOCUMENTS

| | | |
|---|---|---|
| 4,659,330 A | 4/1987 | Nelson et al. |
| 4,664,654 A | 5/1987 | Strauss |
| 4,666,435 A | 5/1987 | Braginetz |
| 4,693,708 A | 9/1987 | Wanderer et al. |
| 4,702,738 A | 10/1987 | Spencer |
| 4,710,170 A | 12/1987 | Haber et al. |
| 4,731,059 A | 3/1988 | Wanderer et al. |
| 4,731,068 A | 3/1988 | Hesse |
| 4,732,162 A | 3/1988 | Martell |
| 4,735,617 A | 4/1988 | Nelson et al. |
| 4,735,618 A | 4/1988 | Hagen |
| 4,742,910 A | 5/1988 | Staebler |
| 4,746,017 A | 5/1988 | Howard et al. |
| 4,747,831 A | 5/1988 | Kulli |
| 4,747,835 A | 5/1988 | Sandhaus |
| 4,747,836 A | 5/1988 | Luther |
| 4,752,290 A | 6/1988 | Schramm |
| 4,758,231 A * | 7/1988 | Haber et al. .............. 600/576 |
| 4,762,516 A | 8/1988 | Luther et al. |
| 4,767,412 A | 8/1988 | Hymanson |
| 4,767,413 A | 8/1988 | Haber et al. |
| 4,778,453 A | 10/1988 | Lopez |
| D298,352 S | 11/1988 | Raines |
| 4,782,841 A | 11/1988 | Lopez |
| 4,790,822 A | 12/1988 | Haining |
| 4,799,926 A | 1/1989 | Haber |
| 4,801,295 A | 1/1989 | Spencer |
| 4,808,169 A | 2/1989 | Haber et al. |
| 4,813,426 A | 3/1989 | Haber et al. |
| 4,813,938 A | 3/1989 | Raulerson |
| 4,816,024 A | 3/1989 | Sitar et al. |
| 4,819,659 A | 4/1989 | Sitar |
| 4,826,488 A | 5/1989 | Nelson et al. |
| 4,826,489 A | 5/1989 | Haber et al. |
| 4,826,491 A | 5/1989 | Schramm |
| 4,828,107 A | 5/1989 | Spencer |
| 4,828,548 A | 5/1989 | Walter |
| 4,832,696 A | 5/1989 | Luther et al. |
| 4,834,717 A | 5/1989 | Haber et al. |
| 4,838,871 A | 6/1989 | Luther |
| 4,840,185 A * | 6/1989 | Hernandez .............. 600/576 |
| 4,842,591 A | 6/1989 | Luther |
| 4,846,811 A | 7/1989 | Vanderhoof |
| 4,850,961 A | 7/1989 | Wanderer et al. |
| 4,850,976 A | 7/1989 | Heinrich et al. |
| 4,852,584 A | 8/1989 | Selby |
| 4,863,435 A | 9/1989 | Sturman et al. |
| 4,863,436 A | 9/1989 | Glick |
| 4,872,552 A | 10/1989 | Unger |
| 4,874,384 A | 10/1989 | Nunez |
| 4,883,469 A | 11/1989 | Glazier |
| 4,887,998 A | 12/1989 | Martin et al. |
| 4,892,525 A | 1/1990 | Hermann, Jr. et al. |
| 4,894,055 A | 1/1990 | Sudnak |
| 4,897,083 A | 1/1990 | Martell |
| 4,898,588 A | 2/1990 | Roberts |
| 4,900,311 A | 2/1990 | Stern et al. |
| 4,903,832 A | 2/1990 | Stewart |
| 4,906,235 A | 3/1990 | Roberts |
| 4,909,794 A | 3/1990 | Haber et al. |
| 4,911,693 A | 3/1990 | Paris |
| 4,915,696 A | 4/1990 | Feimer |
| 4,915,697 A | 4/1990 | DuPont |
| 4,917,673 A | 4/1990 | Coplin |
| 4,919,656 A | 4/1990 | Bracker et al. |
| 4,927,019 A | 5/1990 | Haber et al. |
| 4,927,417 A | 5/1990 | Moncada et al. |
| 4,928,824 A | 5/1990 | Barasch |
| 4,929,241 A | 5/1990 | Kulli |
| 4,931,040 A | 6/1990 | Haber et al. |
| 4,931,048 A | 6/1990 | Lopez |
| 4,932,940 A | 6/1990 | Walker et al. |
| 4,932,946 A | 6/1990 | Shields |
| 4,935,015 A | 6/1990 | Hall |
| 4,943,282 A * | 7/1990 | Page et al. .................. 604/198 |
| 4,944,723 A | 7/1990 | Haber et al. |
| 4,944,728 A | 7/1990 | Carrell et al. |
| 4,944,731 A | 7/1990 | Cole |
| 4,946,447 A | 8/1990 | Hardcastle et al. |
| 4,950,241 A | 8/1990 | Ranford |
| 4,950,252 A | 8/1990 | Luther et al. |
| 4,958,622 A | 9/1990 | Selenke |
| 4,964,854 A | 10/1990 | Luther |
| 4,973,316 A | 11/1990 | Dysarz |
| 4,976,702 A | 12/1990 | Andrews et al. |
| 4,986,813 A | 1/1991 | Blake, III et al. |
| 4,986,819 A | 1/1991 | Sobel |
| 4,988,339 A | 1/1991 | Vadher |
| 4,994,042 A | 2/1991 | Vadher |
| 4,994,044 A | 2/1991 | LoDuca |
| 4,997,422 A | 3/1991 | Chow et al. |
| 5,000,167 A | 3/1991 | Sunderland |
| 5,002,536 A | 3/1991 | Thompson et al. |
| 5,013,304 A | 5/1991 | Russell et al. |
| 5,015,241 A | 5/1991 | Feimer |
| 5,019,045 A | 5/1991 | Lee |
| 5,019,051 A | 5/1991 | Hake |
| 5,024,326 A | 6/1991 | Sandel et al. |
| 5,024,660 A | 6/1991 | McNaughton |
| 5,026,345 A | 6/1991 | Teringo |
| 5,026,354 A | 6/1991 | Kocses |
| 5,030,209 A | 7/1991 | Wanderer et al. |
| 5,030,212 A | 7/1991 | Rose |
| 5,037,400 A | 8/1991 | Curry |
| 5,037,401 A | 8/1991 | DeCamp |
| 5,045,062 A | 9/1991 | Henson |
| 5,046,508 A | 9/1991 | Weissler |
| 5,049,136 A | 9/1991 | Johnson |
| 5,051,109 A | 9/1991 | Simon |
| 5,053,017 A | 10/1991 | Chamuel |
| 5,057,088 A | 10/1991 | Narayanan et al. |
| 5,057,089 A | 10/1991 | Greco |
| 5,059,180 A | 10/1991 | McLees |
| 5,061,249 A | 10/1991 | Campbell |
| 5,066,279 A | 11/1991 | Russell |
| 5,066,281 A | 11/1991 | Stevenson-Michener |
| 5,067,942 A | 11/1991 | Jaffe et al. |
| 5,067,944 A | 11/1991 | Nichols |
| 5,067,946 A | 11/1991 | Zhadanov |
| 5,067,949 A | 11/1991 | Freundlich et al. |
| 5,069,669 A | 12/1991 | Kole |
| 5,078,693 A | 1/1992 | Shine |
| 5,084,019 A | 1/1992 | Gartz |
| 5,086,780 A | 2/1992 | Schmitt |
| 5,088,987 A | 2/1992 | Noonan, Jr. |
| 5,088,988 A | 2/1992 | Talonn et al. |
| 5,092,853 A | 3/1992 | Couvertier, II |
| 5,098,394 A | 3/1992 | Luther |
| 5,098,402 A | 3/1992 | Davis |
| 5,106,379 A | 4/1992 | Leap |
| 5,106,380 A | 4/1992 | Lobello |
| 5,108,378 A | 4/1992 | Firth et al. |
| 5,112,307 A | 5/1992 | Haber et al. |
| 5,112,315 A | 5/1992 | Glover et al. |
| 5,114,404 A | 5/1992 | Paxton et al. |
| 5,116,325 A | 5/1992 | Paterson |
| 5,120,309 A | 6/1992 | Watts |
| 5,122,118 A | 6/1992 | Haber et al. |
| 5,125,898 A | 6/1992 | Kaufhold, Jr. et al. |
| 5,127,910 A | 7/1992 | Talonn et al. |
| 5,135,504 A | 8/1992 | McLees |

| | | |
|---|---|---|
| 5,135,505 A | 8/1992 | Kaufman |
| 5,147,326 A | 9/1992 | Talonn et al. |
| 5,160,326 A | 11/1992 | Talonn et al. |
| 5,163,908 A | 11/1992 | Lambert |
| 5,163,917 A | 11/1992 | Huefner et al. |
| 5,171,300 A | 12/1992 | Blake, III et al. |
| 5,171,303 A | 12/1992 | DeCamp |
| 5,176,640 A | 1/1993 | Nacci et al. |
| 5,176,655 A | 1/1993 | McCormick et al. |
| 5,181,524 A | 1/1993 | Wanderer et al. |
| 5,183,468 A | 2/1993 | McLees |
| 5,188,119 A | 2/1993 | Sunderland |
| 5,188,611 A | 2/1993 | Orgain |
| 5,188,613 A | 2/1993 | Shaw |
| 5,190,526 A | 3/1993 | Murray et al. |
| 5,190,532 A | 3/1993 | Yu |
| 5,195,973 A | 3/1993 | Novick |
| 5,195,975 A | 3/1993 | Castagna |
| 5,195,982 A | 3/1993 | Hoenig |
| 5,195,983 A | 3/1993 | Boese |
| 5,195,992 A | 3/1993 | Dudar et al. |
| 5,195,993 A | 3/1993 | Gianakos |
| 5,197,953 A | 3/1993 | Colonna |
| 5,197,954 A | 3/1993 | Cameron |
| 5,201,718 A | 4/1993 | Whisson |
| 5,215,524 A | 6/1993 | Vallelunga et al. |
| 5,215,525 A | 6/1993 | Sturman |
| 5,215,528 A | 6/1993 | Purdy et al. |
| 5,215,529 A | 6/1993 | Fields et al. |
| 5,215,533 A | 6/1993 | Robb |
| 5,215,534 A | 6/1993 | DeHarde et al. |
| 5,215,535 A | 6/1993 | Gettig et al. |
| 5,217,436 A | 6/1993 | Lampropoulous |
| 5,217,437 A | 6/1993 | Farkas |
| 5,219,333 A | 6/1993 | Saqstetter et al. |
| 5,219,338 A | 6/1993 | Haworth |
| 5,221,262 A | 6/1993 | Kite |
| 5,222,942 A | | 6/1993 | Bader | |
| 5,222,943 A | | 6/1993 | Mazzara | |
| 5,222,944 A | | 6/1993 | Harris | |
| 5,222,945 A | | 6/1993 | Basdnight | |
| 5,222,947 A | | 6/1993 | D'Amico | |
| 5,337,756 A | * | 8/1994 | Barbier et al. | 600/576 |
| 5,338,311 A | | 8/1994 | Mahurkar | 604/195 |
| 5,403,286 A | * | 4/1995 | Lockwood, Jr. | 600/576 |
| 5,423,758 A | * | 6/1995 | Shaw | 600/576 |
| 5,437,639 A | * | 8/1995 | Malenchek | 600/576 |
| 5,514,100 A | | 5/1996 | Mahurkar | 604/195 |
| 5,643,222 A | | 7/1997 | Mahurkar | 604/195 |
| 5,685,862 A | | 11/1997 | Mahurkar | 604/194 |
| 5,762,634 A | * | 6/1998 | Davis | 604/195 |
| 6,106,500 A | * | 8/2000 | Mahurkar | 604/195 |
| 6,117,112 A | * | 9/2000 | Mahurkar | 604/110 |
| 6,280,401 B1 | * | 8/2001 | Mahurkar | 128/919 |

OTHER PUBLICATIONS

Devices & Diagnostics Letter, vol. 19, No. 19 (May 8, 1992).
FDA Medical Bulletin, vol. 22, No. 2 (Sep. 22, 1992).
"Safer Syringes Boost Molder Opportunities" by Carl Kirkland, Plastic World, vol. 51/No. 8, pp. 20–24, (Aug. 1993).
"Ultrasonics Get Medical Seal Of Approval" by Marcie Moskowitz, Plastic World, vol. 51/No. 8, pp. 26–28, (Aug. 1993).
Brochure for Arrow® Ravlerson Syringe.
Brochure for Syringes by Becton Dickinson of Franklin Lakes, New Jersey (1992).
Devices & Diagnostics Letter, p. 2 (Aug. 21, 1992).
Chiarello, Linda A., Reducing Needlestick Injuries among Health Care Workers: AIDS Clinical Care Oct. 1993 V.5 No. 10 Mass. Medical Society.

* cited by examiner

HYPODERMIC NEEDLE ASSEMBLY

CROSS REFERENCE TO RELATED APPLICATIONS

This application is a divisional application of application Ser. No. 08/859,140, filed May 20, 1997 for "Hypodermic Needle Assembly," now U.S. Pat. No. 6,280,401, which is a continuation-in-part of application Ser. No. 08/573,663, filed Dec. 18, 1995, for "Hypodermic Needle Assembly," now U.S. Pat. No. 5,685,862, which is a division of application Ser. No. 08/229,811, filed Apr. 19, 1994, for "Hypodermic Needle Assembly," now U.S. Pat. No. 5,514,100 which was a division of application Ser. No. 08/111,372, filed Aug. 23, 1993, for "Hypodermic Needle Assembly;" now U.S. Pat. No. 5,338,311.

FIELD OF THE INVENTION

The present invention generally relates to hypodermic needle devices for collecting samples of blood or other body tissue. In particular, the present invention relates to such devices that conceal the sharp point of the hypodermic needle following use.

BACKGROUND OF THE INVENTION

A hypodermic needle entering into a patient's body is invariably contaminated by the patient's blood and body fluids. Following use of the needle, the needle presents a risk to physicians, nurses, and other health care personnel because the needle might transmit an infection or disease to such personnel if it were to accidentally puncture them. Thus, health care personnel are in constant danger of contracting infections and diseases, some of which may be deadly. Other potential victims of accidental needle punctures include sanitation workers who later dispose of garbage containing the hypodermic needles. Often a needle puncture in a person's skin is so trivial that it remains unrecognized until the person becomes seriously ill. The diseases which may be transmitted by a contaminated hypodermic needle include Immune Deficiency Virus, Hepatitis, Rabies, Cure, Encephalitis, and Arbor viruses. The outcome of contracting one of these diseases is often fatal because there are no known cures for any of these diseases.

The problem of accidental needle punctures is well recognized, and enormous inventive effort has been devoted to concealing the sharp needle point of hypodermic needles. One such effort is described in the present applicant's U.S. Pat. No. 5,338,311, issued Aug. 16, 1994, and 5,514,100, issued May 7, 1996. A hypodermic needle has many applications in modern medicine. One application is to fit the hypodermic needle onto a syringe so that the needle can be inserted into a person's body or vein to obtain samples of tissue or blood for examination. To obtain multiple samples for different tests, a double-ended hypodermic needle is attached to the syringe barrel. One sharp end of the needle is used to puncture the vein of the patient, while the other sharp end projects inside the syringe barrel. A pre-vacuumed test tube with a rubber stopper is forced on the needle end inside the barrel. Puncture of the rubber stopper results in the withdrawal of a blood sample into the test tube because of the preexisting vacuum. The test tube containing the blood sample is then withdrawn, and another test tube intended for a different test is forced into the barrel to collect a second sample in an identical manner. The barrel with the attached needle is disposed of in its entirety, but during its transport to final destruction it may cause accidental needle sticks and transmit diseases.

The double-ended needles pose special problems because retraction of one sharp end can result in the projection of another sharp end toward the user. Further, the needle may be screwed to the end of the barrel, which makes retraction of the needle difficult or impossible.

SUMMARY OF THE INVENTION

A primary object of the present invention is to provide an improved blood sample collection assembly that conceals the sharp needle point after its use.

One specific object of this invention is to provide an improved blood sample collection assembly which provides good structural stability for the mechanism that is used to retract the needle after it has been used.

Yet another object of the present invention is to provide such an improved blood sample collection assembly which facilitates fabrication, and reduces the cost, of the assembly.

Still another object of the present invention is to provide such an improved blood sample collection assembly which facilitates the operation of the assembly, particularly during retracting movement of the needle.

Another object of the present invention is to provide such an improved blood sample collection assembly which improves the acceptability of the assembly by providing an external appearance which is virtually the same as that of conventional hypodermic needle blood sample collection assemblies which do not provide for needle retraction.

A further object of the invention is to provide such an improved blood sample collection assembly that operates in a fail-safe manner in that the retraction mechanism must be actuated by conscious effort, and the retracting movement automatically stops when both ends of the double-ended needle are concealed.

Other objects and advantages of the invention will become apparent upon reading the following detailed description and upon reference to the accompanying drawings.

In accordance with the present invention, the foregoing objectives are realized by providing a hypodermnic-needle sample collection device comprising an elongated, generally cylindrical barrel forming an aperture at the distal end of the barrel and opening into the interior of the barrel; a needle holder mounted for longitudinal movement within the barrel, the needle holder including a pin projecting laterally therefrom; a hollow needle carried by the needle holder and projecting from the holder along the axis of the barrel; and guide means forming longitudinal linear and spiral guide surfaces extending along at least a portion of the length of the barrel for engaging the pin and moving the needle longitudinally within the barrel in response to relative rotational movement between the linear and spiral guide surfaces.

In a preferred embodiment of the invention, the guide means comprises a guide tube telescoped within the barrel, the opposed walls of the guide tube and barrel forming cooperating spiral and longitudinal slots receiving the laterally projecting pin. The guide tube and barrel are rotatable relative to each other so that one of the side walls of the spiral slot cams the pin along the longitudinal slot when the guide tube and barrel are rotated relative to each other. The guide tube preferably forms the spiral slot, and the barrel forms the longitudinal slot, with the longitudinal slot being open on the interior surface of the barrel and closed on the exterior surface of the barrel, and the pin terminating within the longitudinal slot.

BRIEF DESCRIPTION OF THE DRAWINGS

FIG. 16b is a perspective view showing the manner of assembly of the blood sample collection assembly in FIG. 16a;

DETAILED DESCRIPTION OF THE PREFERRED EMBODIMENTS

While the invention is susceptible to various modifications and alternative forms, specific embodiments thereof have been shown by way of example in the drawings and will be described in detail below. It should be understood, however, that it is not intended to limit the invention to the particular forms disclosed, but on the contrary, the intention is to cover all modifications, equivalents, and alternatives falling within the spirit and scope of the invention as defined by the appended claims.

Figure 1:
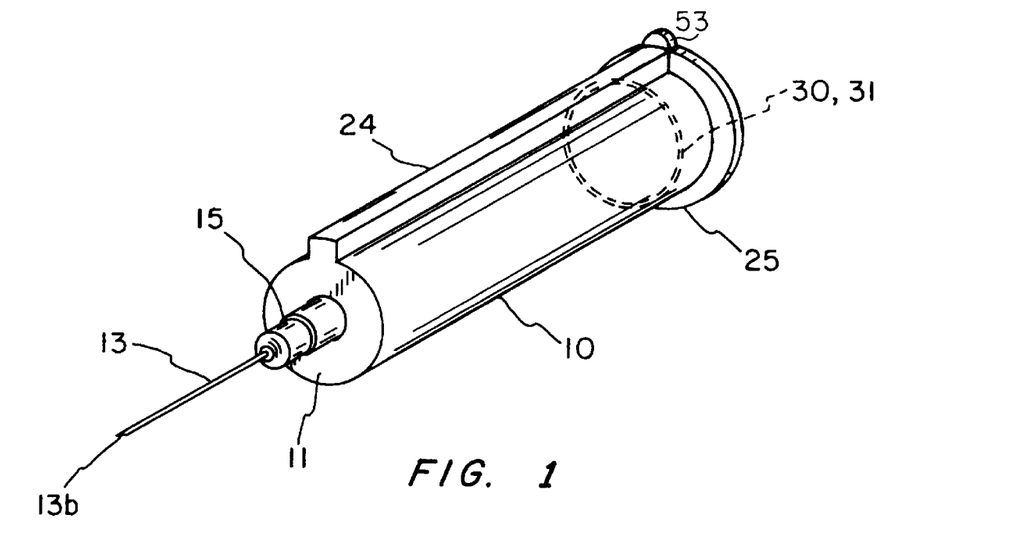
FIG. 1 is a perspective view of a sample collection device embodying the present invention, with the needle fully extended.
Figure 2:
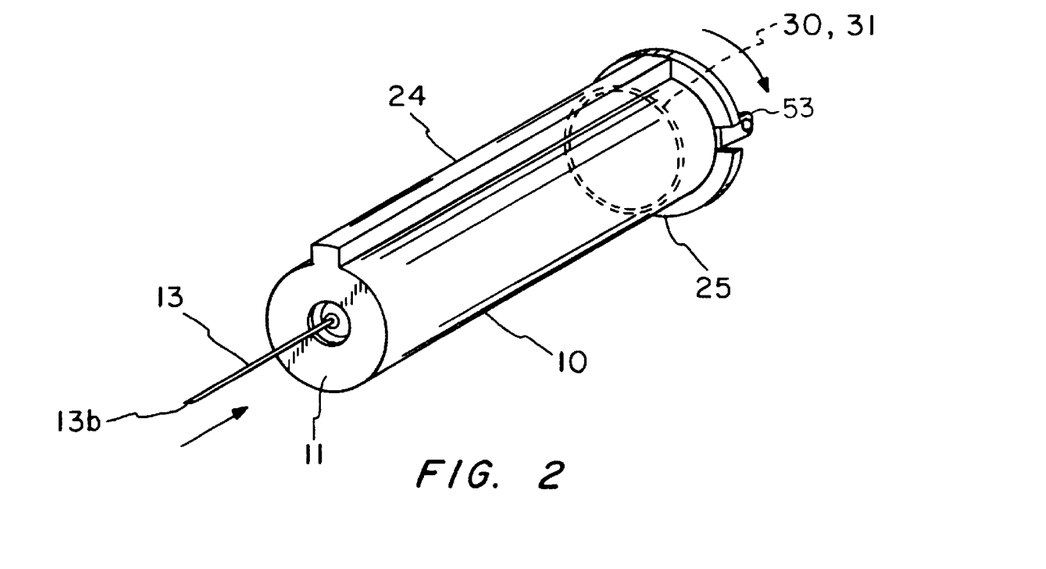
FIG. 2 is the same perspective view shown in FIG. 1, with the needle partially retracted.
Figure 3:
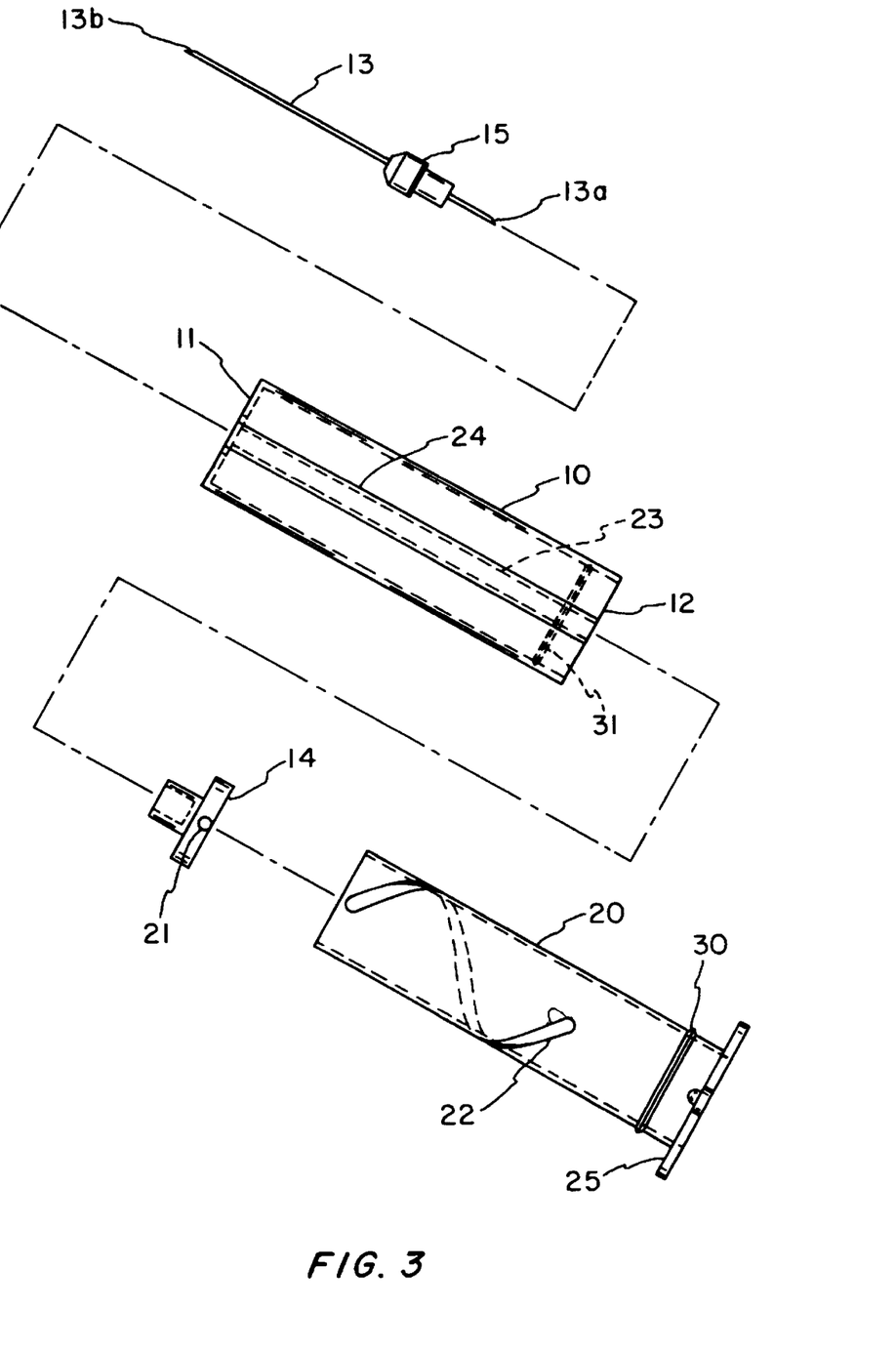
FIG. 3 is an exploded side elevation of the sample collection device shown in FIGS. 1 and 2.
Figure 4:
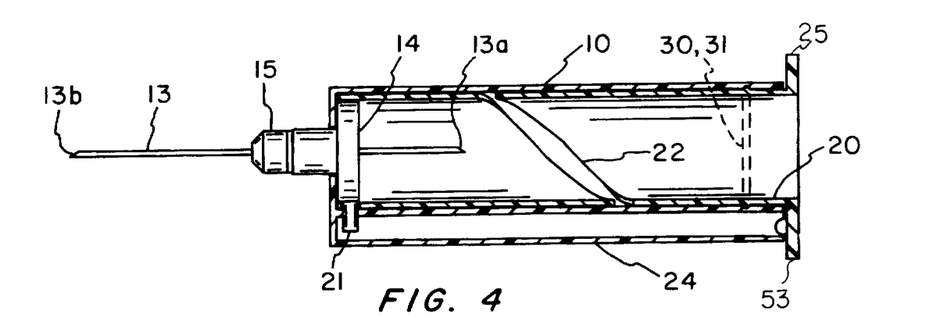
FIG. 4 is an enlarged longitudinal section of the sample collection device of FIGS. 1–3 with the needle in its fully extended position, and showing the needle and needle holder in full elevation.
Figure 5:
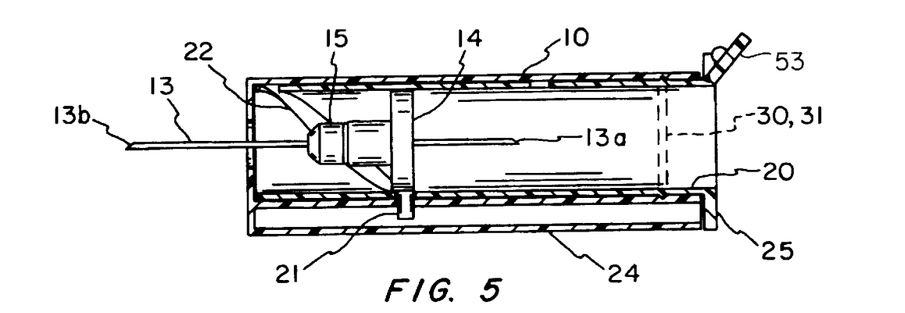
FIG. 5 is the same view shown in FIG. 4 with the needle in a partially retracted position.
Figure 6:
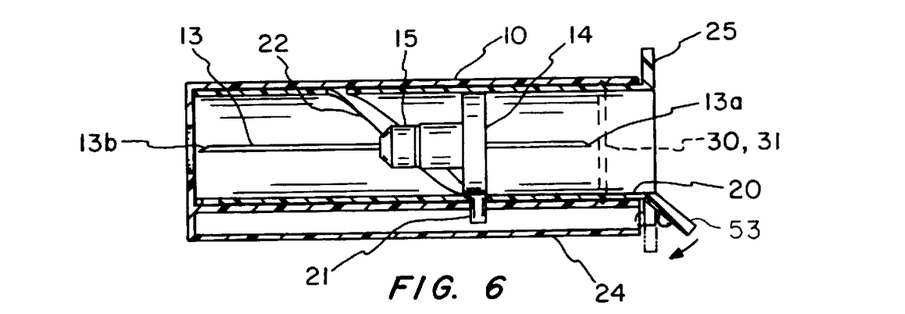
FIG. 6 is the same view shown in FIG. 4 with the needle fully retracted.
Figure 7:
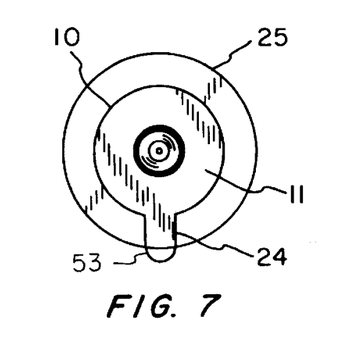
FIG. 7 is an end view generally taken from the left side of FIG. 4.
Figure 8:
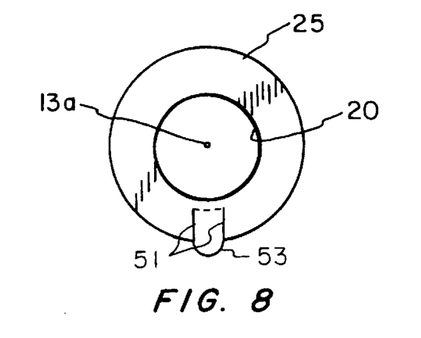
FIG. 8 is an end elevation of the right-hand end of the sample collection device of FIGS. 1–7.

Turning now to the drawings and referring first to FIG. 1, there is shown a blood sample collection device having a cylindrical barrel 10 that forms an apertured end wall 11 at one end, while the other end 12 is open to accept a conventional pre-vacuumed test tube (not shown) to collect samples of blood transmitted by a double-ended needle 13. The needle 13 is carried by a circular needle plate 14 mounted for reciprocating axial movement within the barrel 10. In the illustrative embodiment of FIGS. 1–10, the needle 13 is a conventional double-ended needle having a plastic hub 15 rigidly attached to the needle between the two sharp ends 13a and 13b. The hub 15 is located slightly closer to the proximal end 13a than the distal end 13b so that the length of needle projecting distally from the hub 15 for insertion into the patient is greater than the length of needle projecting proximally from the hub for piercing the test tube.

The mechanism for effecting axial movement of the needle plate 14 within the barrel includes a guide tube 20 telescoped into the barrel 10 and a pin 21 projecting radially from the plate 14 through a spiral slot 22 formed by the tube 20 and extending along a substantial portion of the length of the barrel 10. The outer end of the pin 21 extends through a straight longitudinal slot 23 formed in the wall of the barrel 10. To close the barrel wall to prevent any leakage of blood or other liquid from the interior of the barrel, and to prevent undesired materials from entering the interior of the barrel 10, the slot 23 is covered by a longitudinal channel 24 that may be formed as an integral part of the barrel 10 or as a separate part that is bonded to the barrel wall along the margins of the slot 23. The channel 24 receives the outer end of the pin 21 and permits longitudinal movement of the pin as it passes along the slot 23.

The guide tube 20 is telescoped into the barrel 10 through the open end 12 with the outside wall of the tube 20 sliding along the inside wall of the barrel 10. To permit relative rotational movement between the barrel 10 and the tube 20, their opposed walls are not attached to each, and do not fit so tightly as to inhibit such rotational movement. Relative rotational movement between the barrel 10 and the guide tube 20 causes the pin 21 to be cammed longitudinally along the slot 23 in the wall of the barrel. The pin 21 cannot move in a circumferential direction relative to the barrel 10 because the pin is captured in the longitudinal slot 23. Consequently, rotational movement of the guide tube 20 relative to the barrel 10 causes the walls of the spiral slot 22 in the tube 20 to cam the pin longitudinally along the straight slot 23. Because the pin 21 is an integral part of the needle plate 14, and the needle hub 15 is attached to the plate 14, the needle 13 and its hub 15 and plate 14 all follow the longitudinal movement of the pin 21. Thus, advancing and retracting axial movement of the needle 13 relative to the barrel 10 can be effected by simply turning the guide tube 20 within the barrel 10. To facilitate such turning of the guide tube 20, a knurled flange 25 is formed on the proximal end of the tube 20. The user simply holds the barrel 10 while turning the knurled flange 25.

To retain the guide tube 20 within the barrel 10, the outer surface of the guide tube 20 forms a circumferential rib 30 that snaps into a corresponding groove 31 formed in the inside surface of the barrel 10 when the tube 20 is telescoped into the barrel 10. The fit between the tube 20 and the barrel 10 is sufficiently tight that the interlock between the rib 30 and groove 31 holds the two parts together in the longitudinal direction, unless a substantial axial force is exerted on the two parts to separate them. Yet, because the rib 30 and groove 31 are continuous around the circumferences of the tube 20 and barrel 10, the interlock does not inhibit relative rotational movement between the two parts.

In the illustrative embodiment, the proximal margin of the groove 31 forms a large acute angle (close to 90 degrees) with the base of the groove (see FIG. 9), while the distal margin slopes away from the base of the groove at an obtuse angle. The proximal side of the rib 30 is perpendicular to the axis of the tube 20, while the distal side is tapered with a gradual slope. These shapes facilitate the telescoping of the guide tube 20 into the barrel until the rib 30 snaps into the groove 31, thereby locking the tube 20 and barrel 10 together in the longitudinal direction, while permitting relative rotational movement between them.

The circular needle plate 14 fits snugly inside the guide tube 20 and receives orie end of the hub 15 of the double-ended needle 13. The hub 15 and the plate 14 may be adhesively bonded to each other. The needle plate 14 is provided with substantial margins so that it does not tilt and remains steady within the inner tube.

Figure 9:
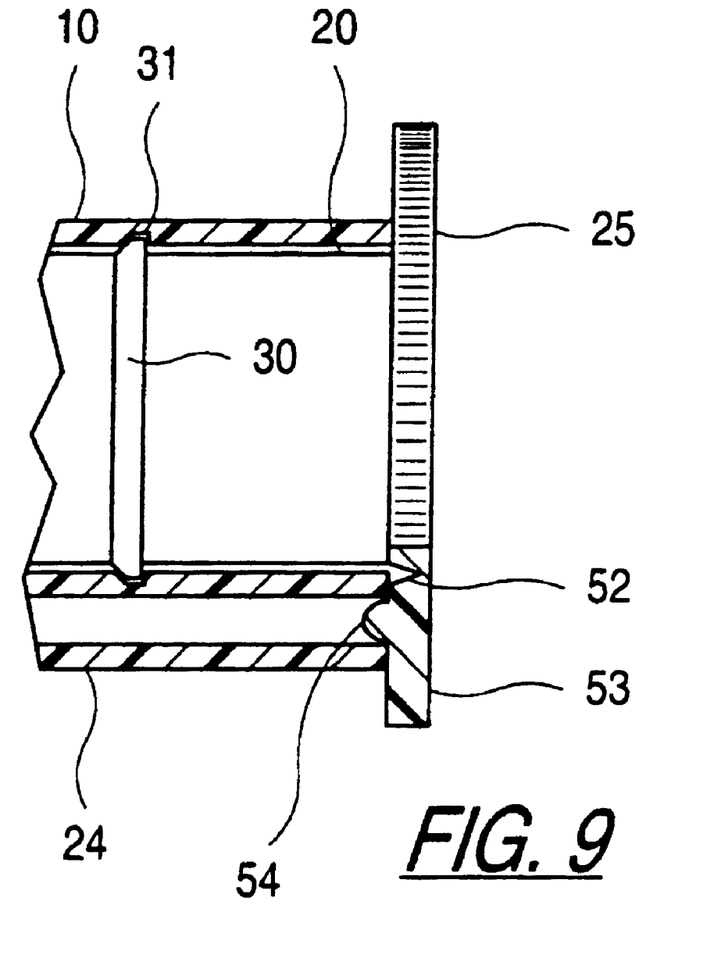
FIG. 9 is an enlarged longitudinal section of a portion of the right-hand end of the sample collection device of FIGS. 1–8, with the guide tube shown in full elevation.

In order to lock the needle 13 in either its fully advanced or fully retracted position, a latch is provided to lock the guide tube 20 to the barrel 10 in the circumferential direction so that these two members cannot be rotated relative to each other. In the illustrative embodiment, this latch is formed as an integral part of the flange 25 on the proximal end of the guide tube 20. Thus, a pair of parallel slits 51 extend inwardly from the outer edge of the flange 25 to a living hinge 52. This forms a small rectangular tab 53 which can be pivoted away from the end of the barrel 10. This tab 53 is positioned directly over the end of the channel 24, and the distal surface of the tab 53 forms a small bead 54 which fits into the open interior of the channel 24 with a frictional fit. When the tab 53 is in this latched position, as illustrated in FIG. 9, the interlocking engagement of the bead 54 with the interior walls of the channel 24 prevents relative rotational movement between the barrel 10 and the guide tube 20. When it is desired to unlatch these two members to permit relative rotational movement therebetween, the tab 53 is pivoted outwardly away from the end of the barrel 10 to remove the bead 54 from the interior of the channel 24. The tab 53 is moved to this unlatched position whenever it is desired to advance or retract the needle holder 14 within the barrel 10.

Figure 10:
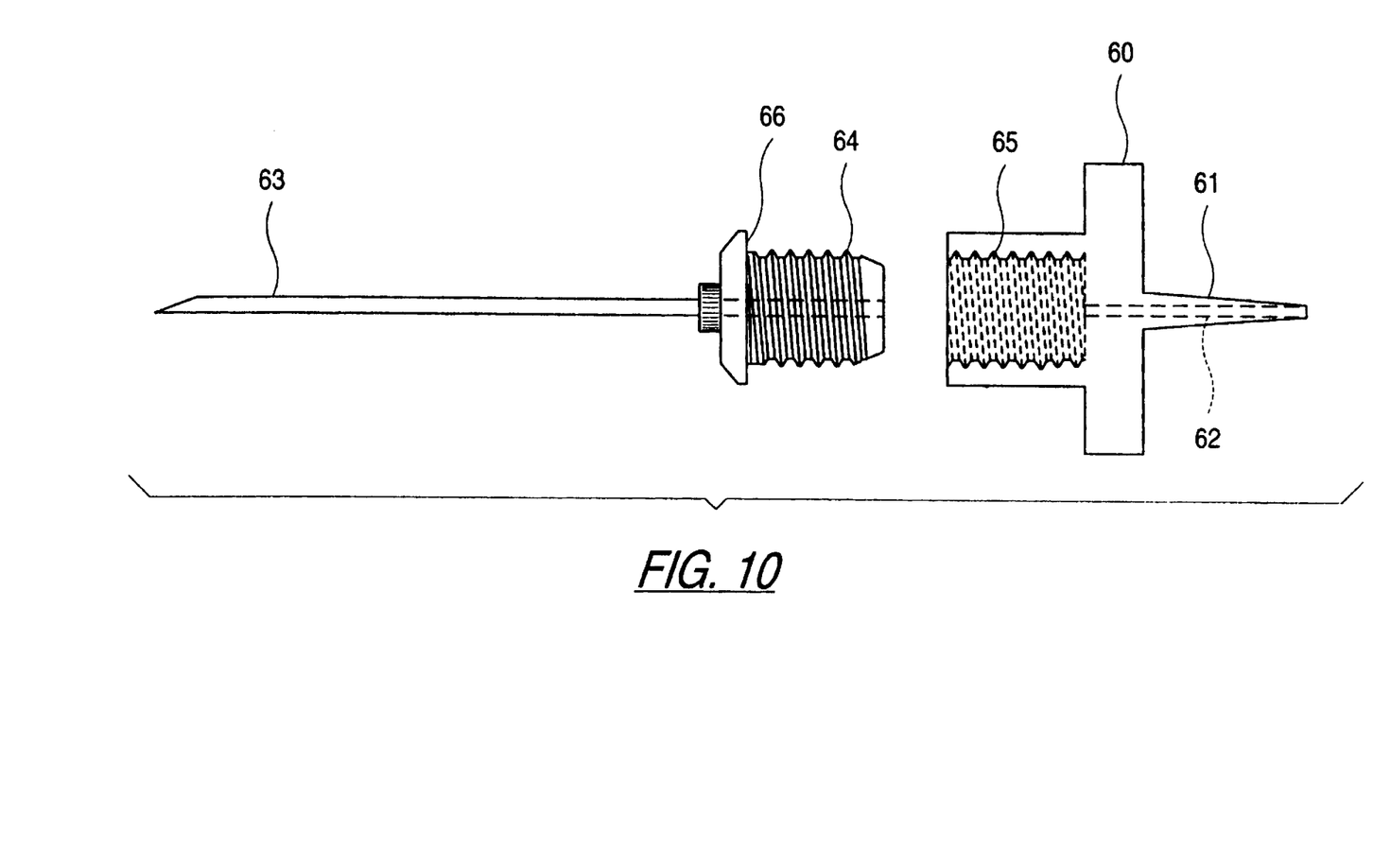
FIG. 10 is an enlarged, exploded side elevation of a modified needle subassembly and needle holder for use in the sample collection device of FIGS. 1–9.
Figure 11:
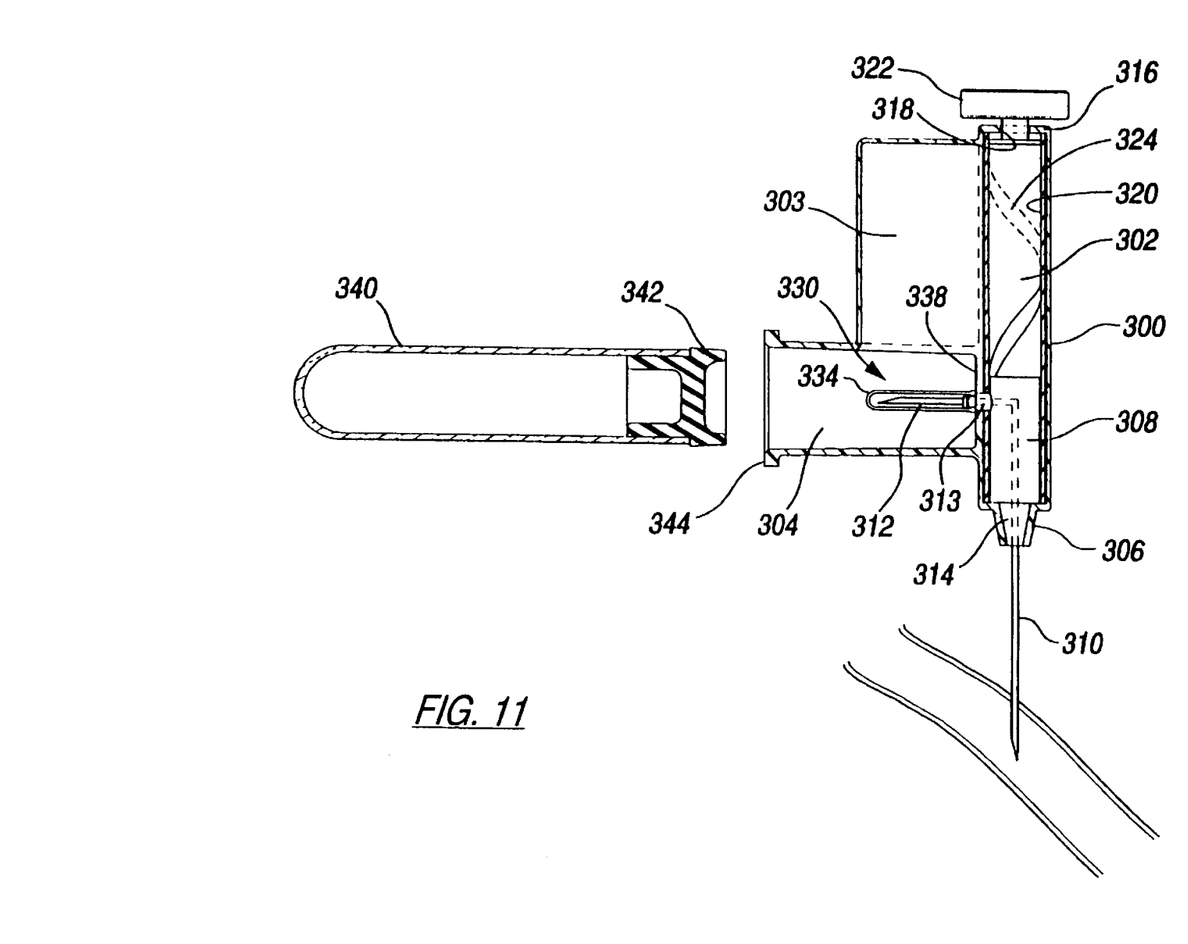
FIG. 11 is a longitudinal section of a blood sample collection assembly embodying the present invention.

FIG. 10 illustrates a modified needle holder 60 which eliminates the need for a double-ended needle. In this case, the needle holder 60 itself forms a tapered stem 61 which is sufficiently sharp to penetrate the rubber stopper in the end of a pre-vacuumed sample collection tube. The rubber stopper in these pre-vacuumed tubes is typically pre-slit, and thus the tapered stem 61 is sufficiently sharp to penetrate the rubber stopper. An internal longitudinal passageway 62 within the tapered stem 61 communicates with the hollow interior of the needle 63 which is fastened to the distal end of the needle holder.

The needle holder 60 in FIG. 10 also includes a modified arrangement for mounting the needle 63 in the needle holder. In this modified arrangement, the needle 63 is mounted on, and extends through, a hub having a threaded external surface 64 which mates with a threaded bore 65 in the distal end of the main body of the needle holder 60. The hub also includes a flange 66 which seats against the distal end surface of the needle holder 60 when the hub is fully threaded into the bore 65.

To use the illustrative sample collection device, the patient's skin is cleansed with isopropyl alcohol, the vein is made prominent by a torniquet and then the vein is punctured by the needle. When the needle is felt to be in the vein, the blood sample collection unit is stabilized and a pre-vacuumed test tube is advanced into the barrel in an inverted position. The end of the needle inside the barrel punctures the rubber cap of the test tube and fills the test tube as a result of vacuum inside the tube. Once filled the tube is removed and additional tubes are inserted into the barrel to obtain additional diagnostic samples.

After the required number of samples have been obtained, the needle is withdrawn and the bleeding puncture area is compressed and taped. Holding the sample collection device by one hand, the living hinge latch on the margin of the guide tube is released, and the guide tube is then rotated for a single turn. The guide tube stops automatically after one full turn, and both ends of the needle are now concealed within the barrel of the blood sample collection device. This is achieved by a specific length of the spiral slot that stops at a predetermined location. The latch is then closed to lock the needle device securely at this location, and the device is then disposed of The components of the sample collection device can be made by conventional methods of machining steel tubing, and injection molding by using medical grade polymers such as polypropylene and others for barrel, plunger and latch components. The plunger seal or cap is molded from natural or synthetic elastomeric. The spiral sleeve is molded conventionally from polypropylene by using two slides and a core pin, and is press fit and locked with detentes into the wider proximal part of the barrel. Alternatively, molding of the spiral slot can be performed by rotating cores with elevated spiral. After molding the spiral around the cores, the cores are removed while simultaneously rotating them. The linear channel in the barrel is molded by press fitting a plate in the core pin and providing an identical channel in the cavity of the barrel. The needle plate with molded thread and arm are molded from polypropylene.

Another embodiment of the present invention, illustrated in FIGS. 11–16b, provides a blood sample collection assembly including an integral external body 300 forming a first needle chamber 302, a second needle chamber 303, and a vacuum tube chamber 304. The axis of the first needle chamber 302 is orthogonal to the axis of the vacuum tube chamber 304. The first needle chamber 302 is a tubular or square hollow body having a hollow tapered conical nozzle 306 integrally connected to the distal end thereof. The nozzle 306 forms a locking female luer taper. The interior of the conical nozzle 306 communicates with the interior of the first needle chamber 302.

A cylindrical needle holder 308, having either a double-ended hypodermic needle with a ninety degree bend or a pair of orthogonal hypodermic needles 310, 312 mounted therein, is disposed within the first needle chamber 302. The needle holder 308 is displaceably interlocked to the first needle chamber 302 by a taper lock between the conically tapered portion 314 of the needle holder 308 and the nozzle 306. The needle 310 protrudes from the distal end of the needle holder 308 and is coaxial with the first needle chamber 302. Prior to using the blood sample collection assembly, the needle 310 is covered by a conventional protective cap (not shown) to prevent the sharp beveled point of the needle 310 from accidentally puncturing someone. The needle 310 projects approximately one and one-quarter inches from the tapered portion 314 of the needle holder 308.

The other needle 312 is integrally connected to and mounted ninety degrees away from the needle 310. During normal use, the needle 312 is positioned along the axis of the vacuum tube chamber 304 and the needle 312 protrudes from a side arm 313 of the needle holder 308 into the vacuum tube chamber 304 at its base 338. In one embodiment, the needle 312 is a metallic hypodermic needle capable of penetrating a rubber stopper of a conventional vacuum tube. Alternatively, the needle 312 may be composed of plastic capable of penetrating a rubber stopper but incapable of penetrating skin, thereby eliminating the need for the second needle chamber 303. Such a plastic needle is manufactured and distributed by Baxter International of Deerfield, Illinois. The use of the plastic needle reduces the possibility of accidental needle punctures by one-half Since both of the needles 310, 312 are hollow, the interior of the needle 310 communicates with the interior of the needle 312 to form a continuous flow path between the needles.

Figure 13:
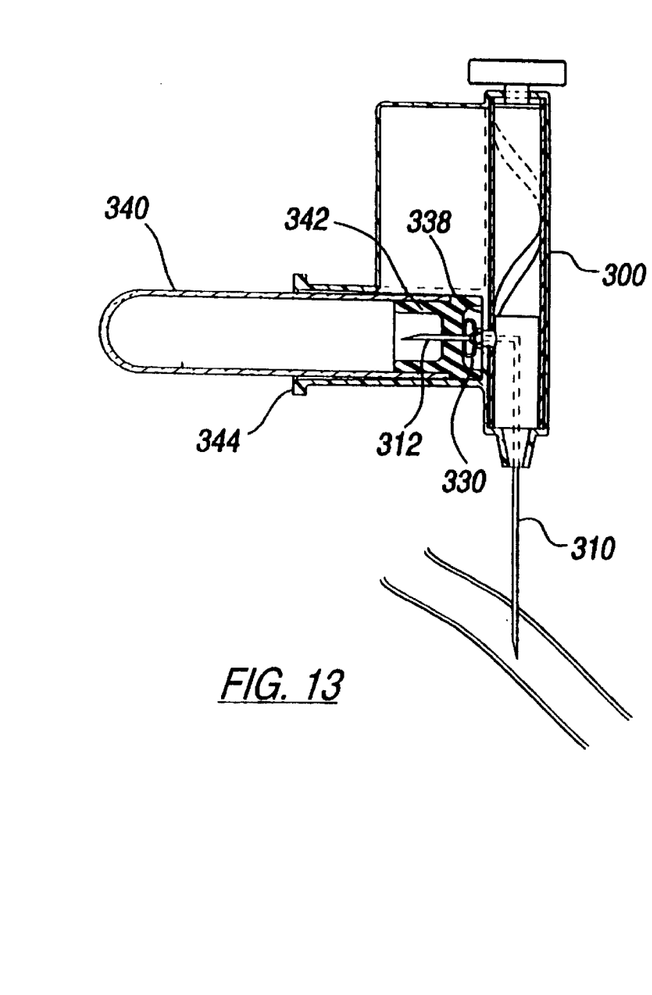
FIG. 13 is a longitudinal section of the blood sample collection assembly in FIG. 11 with the vacuum tube completely advanced within the vacuum tube chamber so that a needle of the assembly pierces the rubber stopper of the vacuum tube.
Figure 16A:
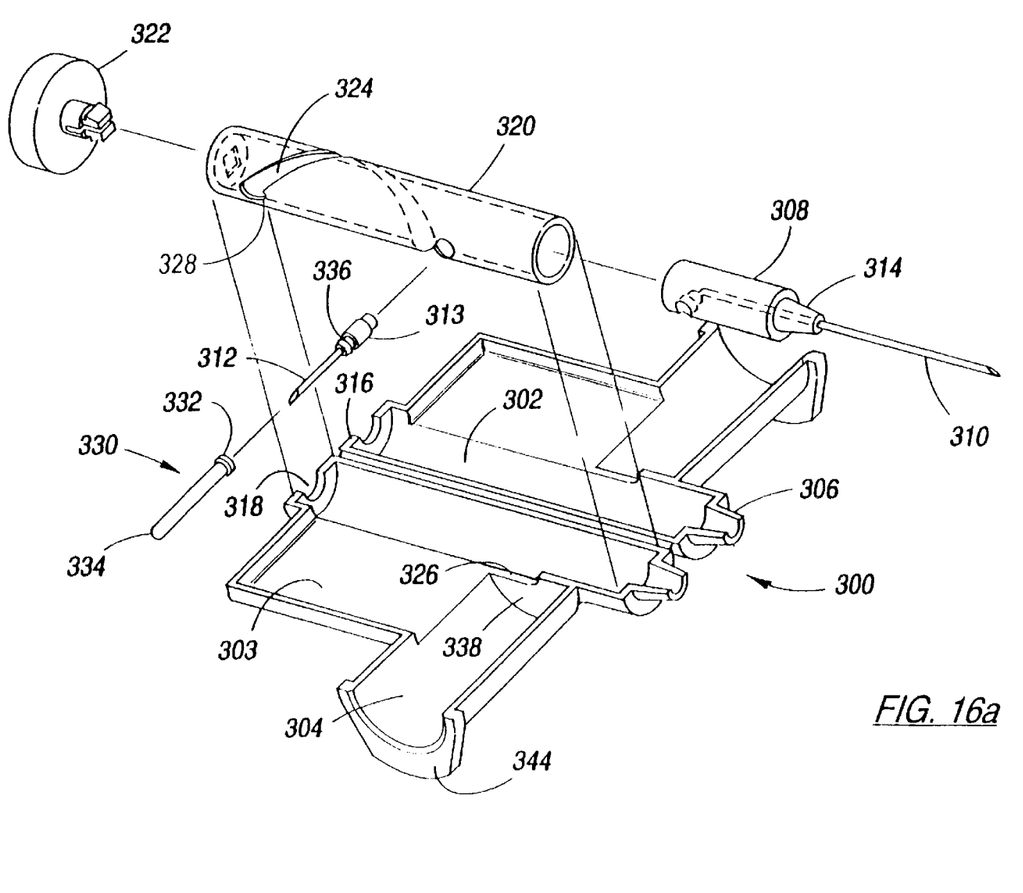
FIG. 16a is an exploded perspective view of the blood sample collection assembly in FIG. 11 showing that the external body is thermoformed from two polymeric constructions which are mirror images of one another.

The needle 312 is covered by a self-sealing rubber cap 330 having an open end 332 and a closed end 334 (FIG. 16a). The rubber cap 330 is retained in place by a plastic retaining ring 336 mounted on the circumference of the needle 312 (FIG. 16a). As a vacuum tube 340 is inserted into the vacuum tube chamber 304, the rubber stopper 342 of the vacuum tube 340 depresses the cap 330 so that the needle 312 pierces both the closed end 334 of the cap 330 and the rubber stopper 342 (FIG. 13). This allows blood entering the needles 310, 312 to pass into the vacuum tube 340. As the vacuum tube 340 is removed from the vacuum tube chamber 304, the cap 330 springs back to its position covering the needle 312 so as to check the flow of blood exiting from the needle 312. Thus, the rubber cap 330 acts as a valve which is opened by inserting a vacuum tube 340 into the vacuum tube chamber 304 and which is closed by removing the vacuum tube 340 from the vacuum tube chamber 304. The vacuum tube 340 recited herein may be any glass or plastic tube or tubular stem of a flask that is closed by a rubber stopper and contains a vacuum.

Figure 15:
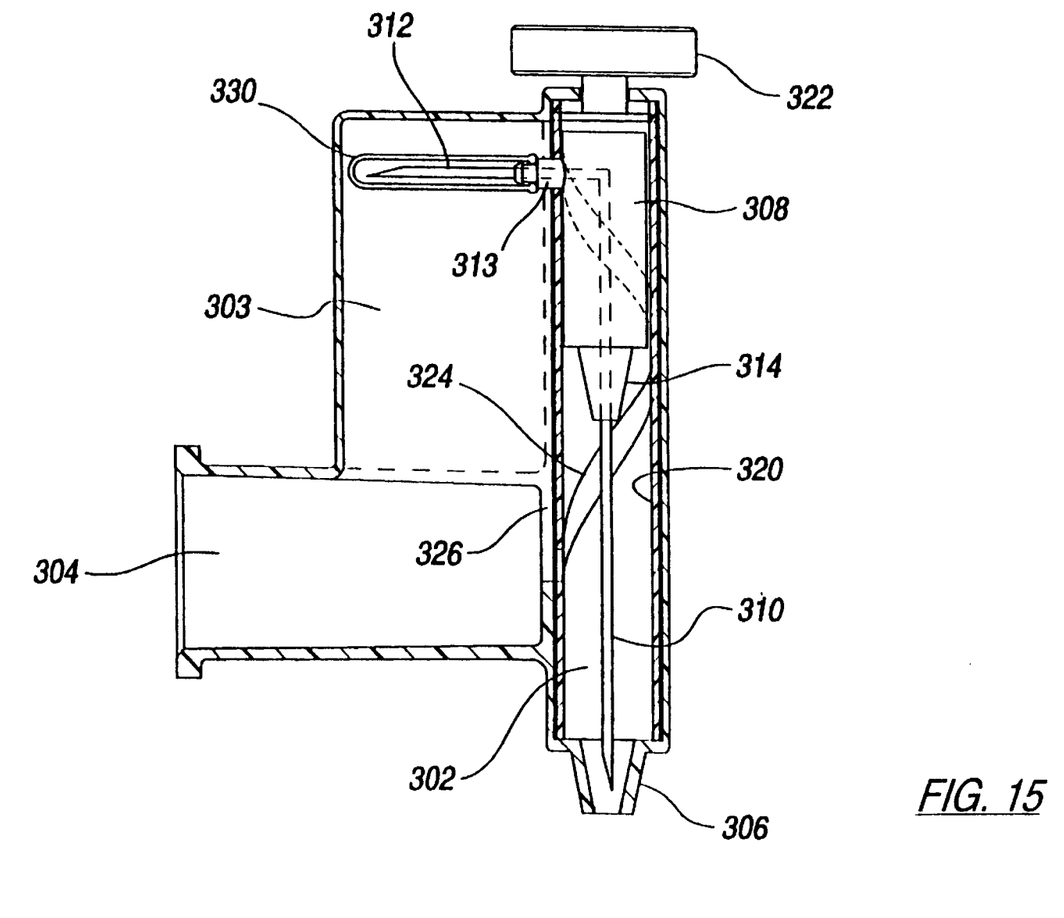
FIG. 15 is a longitudinal section of the blood sample collection assembly in FIG. 11 with the needle holder and mounted needles in the retracted position.

Following normal use of the blood sample collection assembly, the needle holder 308 is retracted toward the proximal end of the first needle chamber 302, thereby causing the needle 312 to retract into the second needle chamber 303 (FIG. 15). The second needle chamber 303 is preferably a generally rectangular body which is narrow in one transverse direction and relatively wide in the other transverse direction (see FIGS. 16a–16b). The transverse dimensions are sufficiently wide to accommodate the width and length of the needle 312. The longitudinal dimension of the second needle chamber 303 is sufficiently long to accommodate the needle 312 when the needle holder 308 is fully retracted within the first needle chamber 302.

At the proximal end, the first needle chamber 302 forms a lid 316 having a circular lid aperture 318. Furthermore, an internal tube 320 is disposed within the first needle chamber 302, and the tube 320 is connected to a circular knob 322 via the lid aperture 318. Both the tube 320 and the circular knob 322 are coaxial with the first needle chamber 302, and rotation of the circular knob 322 relative to the first needle chamber 302 causes the tube 320 to rotate relative to the first needle chamber 302. The circular knob 322 preferably includes a textured longitudinal surface to permit the knob 322 to be easily gripped and rotated. The length of the internal tube 320 matches the internal longitudinal dimension of the first needle chamber 302 to prevent axial movement of the tube 320 relative to the first needle chamber 302. Moreover, the outer diameter of the internal tube 320 is slightly smaller than the inner diameter of the first needle chamber 302 to permit the internal tube 320 to rotate freely, yet stably, relative to the first needle chamber 302.

Figure 14A:
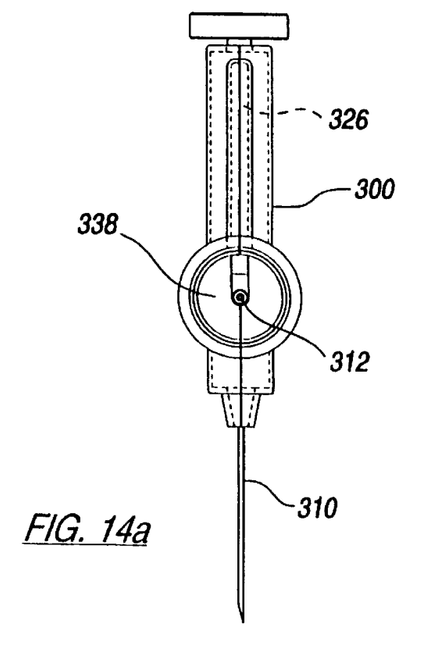
FIG. 14a is a side plan view, taken orthogonal to the longitudinal sections in FIGS. 11–13, of the blood sample collection assembly embodying the present invention.
Figure 14B:
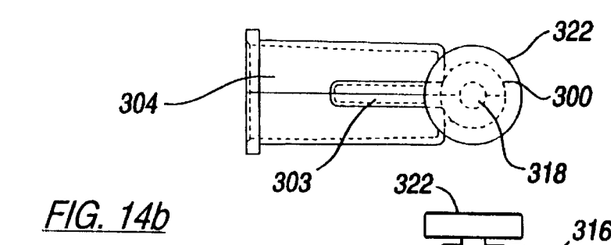
FIG. 14b is a top plan view of the blood sample collection assembly in FIG. 11.
Figure 14C:
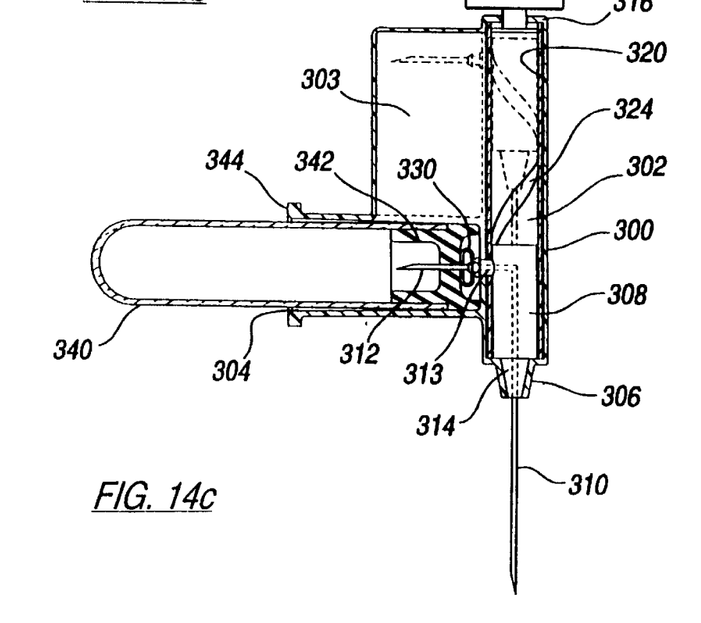
FIG. 14c is a longitudinal section of the blood sample collection assembly in FIG. 11 with the needle holder and mounted needles being shown in the forward position (solid lines) and the retracted position (dotted lines)

Rotation of the internal tube 320 relative to the first needle chamber 302 causes the needle holder 308 to move axially within the first needle chamber 302 from a forward position to a retracted position. In FIG. 14c, the forward position of the needle holder 308 is depicted in solid lines, while the retracted position is depicted in dotted lines. Axial movement of the needle holder 308 relative to the first needle chamber 302 is effected using a helical slot 324 in the circumferential wall of the internal tube 320 in conjunction with a longitudinal slot 326 in the wall of the first needle chamber 302. The helical slot 324 and longitudinal slot 326 are positioned such that the side arm 313 of the needle holder 308 extends through both the distal end of the helical slot 324 and the distal end of the longitudinal slot 326 when the needle holder 308 is in the forward position (FIG. 14a). Similarly, when the needle holder 308 is in the retracted position, the side arm 313 extends through both the proximal end of the helical slot 324 and the proximal end of the longitudinal slot 326. From the foregoing arrangement, it can be seen that the distal end of the longitudinal slot 326 overlies the distal end of the helical slot 324 when the needle holder 308 is in the forward position, and the proximal end of the longitudinal slot 326 overlies the proximal end of the helical slot 324 when the needle holder 308 is in the retracted position.

During retraction of the needle holder 308, the first needle chamber 302 is held stationary while the internal tube 320 is rotated using the circular knob 322. While the internal tube 320 is being rotated, the needle holder 308 is prevented from rotating with the internal tube 320 by virtue of the extension of the side arm 313 through the longitudinal slot 326 in the first needle chamber 302. Instead of rotating, the needle holder 308 moves axially through the first needle chamber 302. More specifically, axial movement of the needle holder 308 is controlled by the movement of the side arm 313 through the helical slot 324 in the rotating tube 320. As the side arm 313 moves through the helical slot 324, the side arm 313 cannot rotate or "swing" with the internal tube 320 because the side arm 313 is lodged in the longitudinal slot 326. Instead, the side arm 313 is forced to ascend the longitudinal slot 326 until the side arm 313 reaches the proximal end of the helical slot 324 (FIG. 15). At the proximal end of the helical slot 324, there is a detente 328 for engaging the ascending side arm 313, thereby locking the needle holder 308 in the retracted position.

Figure 12:
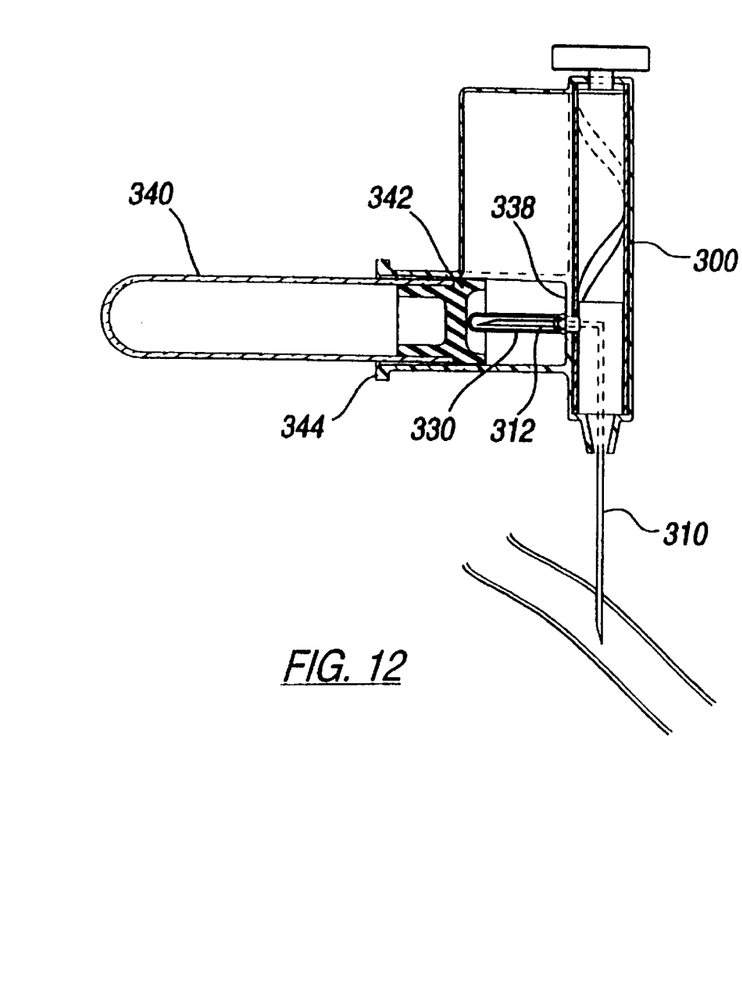
FIG. 12 is a longitudinal section of the blood sample collection assembly in FIG. 11 with the vacuum tube partially advanced within the vacuum tube chamber.
Figure 16B:
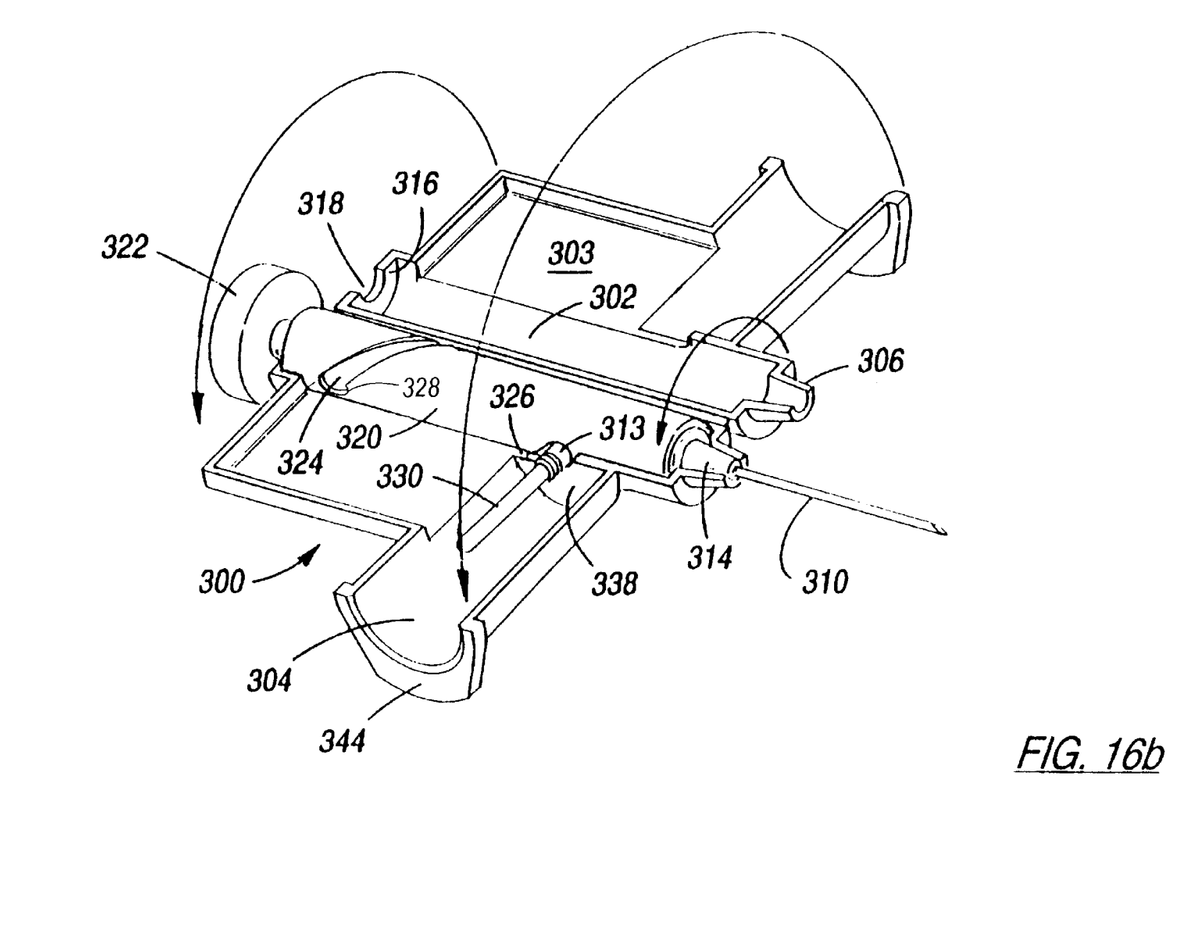

To operate the blood sample collection assembly, the protective cap is removed, the blood sample collection site on the body of a patient is determined, and the skin is cleaned with an antiseptic solution. The needle 310 is then entered into the vein of the patient. To collect a blood sample, the vacuum tube 340 with the rubber stopper 342 is inserted into the vacuum tube chamber 304 (FIGS. 12–13). After the vacuum tube 340 is filled with the desired amount of blood, the vacuum tube 340 is removed from the vacuum tube chamber 304. Additional blood may be collected by inserting, filing, and removing additional vacuum tubes. The vacuum tube chamber 304 includes tabs 344 for providing leverage while pushing a vacuum tube over the point of the needle 312 to puncture the rubber stopper of the vacuum tube. While inserting a vacuum tube, the orthogonal orientation of the vacuum tube chamber 304 relative to the first needle chamber 302 compels that the vacuum tube be pushed into the vacuum tube chamber 304 in a direction toward a stabilizing hand, rather in the direction of the sharp point of the needle 310 located in the vein. Next, the needle 310 is withdrawn from the vein. The circular knob 322 is rotated until the needle holder 308 is completely retracted with the side arm 313 locked in the detente 328 (FIGS. 16a and 16b). With the needle holder 308 in the retracted position, the needle 310 is concealed by the first needle chamber 302 and the needle 312 is concealed by the second needle chamber 303. Finally, the blood sample collection assembly is discarded in its entirety.

It can be seen from the foregoing description that the blood sample collection assembly avoid the situation of advancement of one sharp point of a double-pointed needle towards an operator while retraction of another point of the double-pointed needle is attempted. In particular, since the needle 312 is orthogonal to the needle 310, the side of the needle 312, instead of the point of the needle 312, is advanced toward an operator while the needle 310 is retracted into the first needle chamber 302. Moreover, both needles 310, 312 are retracted and concealed by operating a single mechanism, the circular knob 322. Due to the orthogonal orientation of the vacuum tube chamber 304 relative to the first needle chamber 302, insertion of a vacuum tube is accomplished by pushing the vacuum tube in the direction of a stabilizing hand of an operator, rather than in the direction of the needle in the vein. This reduces the possibility of imparting forward thrust on the needle in the vein which, in turn, minimizes the possibility of double puncturing the vein. Furthermore, the blood sample collection assembly is compact because the needle holder 308 is retracted directly into the internal tube 320 itself Because the needle holder 308 retracts into the internal tube 320, the internal tube 320 need not extended beyond the proximal end of the first needle chamber 302 for needle retraction to occur. Thus, when discarded following use, blood sample collection assembly contributes minimally to the bulk of refuse. The blood sample collection assembly is also compact because, with the needles 310, 312 mounted orthogonal to one another, the length of the assembly is shorter than existing blood sample collection assemblies.

Referring to FIGS. 16a–16b, the blood sample collection assembly is constructed by injection molding the entire assembly from organic polymers, preferably thermoplastics such as a polypropeline or ABS. To construct the needle chambers 302, 303 and the vacuum tube chamber 304, a polymeric sheet is thermoformed to represent a single piece, mirror image, isometric half of these elements. Next, the internal tube 320 with the mounted knob 322 and the needle holder 308 with the mounted needles 310, 312 are positioned at the proper location on the thermoformed sheet, and the thermoformed sheet is folded and secured shut by interlocking detents on the contacting surfaces (FIG. 16b). For additional safety an ultrasonic or solvent bond is created at the areas of contact to maintain the integrity of the assembly. The assembly is sterilized by conventional means.

What is claimed is:

1. A blood sample collection assembly operable in a normal mode and convertible to a retraction mode, comprising:
   a first chamber forming a hollow nozzle located at the distal end of said first chamber and opening into the interior of said first chamber;
   a vacuum tube chamber connected to said first chamber and positioned substantially orthogonal to said first chamber, said vacuum tube chamber having an open end for receiving a vacuum tube;
   a needle holder carrying a first hollow needle on the distal end thereof and carrying a second hollow needle substantially orthogonal to said first hollow needle, said second hollow needle being in fluid communication with said first hollow needle, said second hollow needle extending into said vacuum tube chamber, said needle holder being slidably mounted in said first chamber, said needle holder being detachably engaged to said first chamber with the distal portion of said needle holder being disposed within said nozzle of said first chamber during the normal mode; and
   retraction means for disengaging said needle holder from said first chamber to switch the assembly from the normal mode to the retraction mode and for retracting said needle holder into the first chamber such that said first needle is concealed within said first chamber.

2. The blood sample collection assembly of claim 1, further including a second chamber adjacent to said first chamber, and wherein said retraction means conceals said second needle within said second chamber.

3. The blood sample collection assembly of claim 1, wherein said retraction means includes retainer means for limiting rotation of said needle holder relative to said first chamber.

4. The blood sample collection assembly of claim 3, further including a hollow tube rotatably mounted within said first chamber, said needle holder being disposed within said hollow tube, and wherein said retraction means is responsive to rotation of said hollow tube to retract said needle holder within said hollow tube.

5. The blood sample collection assembly of claim 4, wherein said retraction means includes a helical slot in said hollow tube, and wherein said needle holder includes a side arm extending from a side wall of said needle holder through said helical slot, said second needle being mounted on said side arm, rotation of said hollow tube relative to said first chamber disengaging said needle holder from said nozzle of said first chamber and guiding said side arm of said needle holder proximally through said helical slot, thereby retracting said needle holder into said hollow tube.

6. The blood sample collection assembly of claim 5, wherein said first chamber includes a longitudinal slot opening into said second chamber and said vacuum tube chamber, said side arm extending through said helical slot in said hollow tube and said longitudinal slot in said first chamber, and wherein rotation of said hollow tube relative to said first chamber guides said side arm proximally through said helical slot and said longitudinal slot, said longitudinal slot preventing said needle holder from rotating relative to said first chamber.

7. The blood sample collection assembly of claim 5, wherein said hollow tube includes a detente, disposed at the proximal end of said helical slot, for engaging said side arm to lock said needle holder in a retracted position.

8. The blood sample collection assembly of claim 4, further including a knob mounted on the proximal end of said hollow tube to rotate said hollow tube.

9. The blood sample collection assembly of claim 1, wherein said open end of said vacuum tube chamber includes tabs to facilitate the insertion and removal of the vacuum tube.

10. The blood sample collection assembly of claim 1, wherein said second needle includes a self-sealing rubber cap opened by inserting the vacuum tube into said vacuum tube chamber and closed by removing the vacuum tube from said vacuum tube chamber.

11. The blood sample collection assembly of claim 1, wherein said needle holder includes a tapered male luer at the distal end thereof, and wherein said male luer is detachably engaged within said nozzle by a taper lock.

12. The blood sample collection assembly of claim 1, wherein said second hollow needle is composed of plastic.

13. A blood sample collection assembly operable in a normal mode and convertible to a retraction mode, comprising:
- a first chamber forming a hollow nozzle located at the distal end of said first chamber and opening into the interior of said first chamber;
- a vacuum tube chamber connected to said first chamber, said vacuum tube chamber having an open end for receiving a vacuum tube;
- a needle holder carrying a first hollow needle on the distal end thereof and carrying a second hollow needle extending into said vacuum tube chamber, said second hollow needle being in fluid communication with said first hollow needle, said needle holder being slidably mounted in said first chamber, said needle holder detachably engaging said first chamber with the distal portion of said needle holder disposed within said nozzle of said first chamber during the normal mode;
- a hollow tube rotatably mounted within said first chamber, said needle holder being disposed within said hollow tube; and
- retraction means, responsive to rotation of said hollow tube, for disengaging said needle holder from said first chamber to switch the assembly from the normal mode to the retraction mode and for retracting said needle holder into said hollow tube such that said first needle is concealed within said first chamber.

14. The blood sample collection assembly of claim 13, further including a second chamber adjacent to said first chamber, and wherein said retraction means conceals said second needle within said second chamber.

15. The blood sample collection assembly of claim 13, wherein said retraction means includes retainer means for limiting rotation of said needle holder relative to said first chamber in response to rotation of said hollow tube relative to said first chamber.

16. The blood sample collection assembly of claim 15, wherein said retraction means includes a helical slot in said hollow tube, and wherein said needle holder includes a side arm extending from said needle holder through said helical slot, said second needle being mounted on said side arm, rotation of said hollow tube relative to said first chamber disengaging said needle holder from said nozzle of said first chamber and guiding said side arm of said needle holder proximally through said helical slot, thereby retracting said needle holder into said hollow tube.

17. The blood sample collection assembly of claim 16, wherein said first chamber includes a longitudinal slot opening into said second chamber and said vacuum tube chamber, said side arm extending through said helical slot in said hollow tube and said longitudinal slot in said first chamber, and wherein rotation of said hollow tube relative to said first chamber guides said side arm proximally through said helical slot and said longitudinal slot, said longitudinal slot preventing said needle holder from rotating relative to said first chamber.

18. The blood sample collection assembly of claim 16, wherein said hollow tube includes a detente, disposed at the proximal end of said helical slot, for engaging said side arm to lock said needle holder in a retracted position.

19. The blood sample collection assembly of claim 13, wherein said open end of said vacuum tube chamber includes tabs to facilitate the insertion and removal of the vacuum tube.

20. The blood sample collection assembly of claim 13, wherein said second needle includes a self-sealing rubber cap opened by inserting the vacuum tube into said vacuum tube chamber and closed by removing the vacuum tube from said vacuum tube chamber.

21. The blood sample collection assembly of claim 13, further including a knob mounted on the proximal end of said hollow tube to rotate said hollow tube.

22. The blood sample collection assembly of claim 13, wherein said needle holder includes a tapered male luer at the distal end thereof, and wherein said male luer is detachably engaged within said nozzle by a taper lock.

23. The blood sample collection assembly of claim 13, wherein said vacuum tube chamber is positioned substantially orthogonal to said first chamber, and wherein said second needle is positioned substantially orthogonal to said first needle.

24. In a blood sample collection assembly using a first chamber, a second chamber adjacent to the first chamber, a vacuum tube chamber connected to the first chamber, a hollow tube rotatably mounted in the first chamber, a needle holder detachably lockable to the first chamber and threadably engagable to the hollow tube, and a pair of hollow communicating needles mounted on the needle holder, the method comprising the steps of:
- detachably locking the needle holder to the first chamber;
- rotating the hollow tube relative to the first chamber to unlock the needle holder from the first chamber such that the needle holder is longitudinally movable relative to the first chamber;
- securing the needle holder to the first chamber to prevent rotation of the needle holder relative to the first chamber while the hollow tube is being rotated relative to the first chamber; and
- further rotating the hollow tube to threadably retract the needle holder inside the hollow tube until one of the pair of needles is concealed by the first chamber and the other of the pair of needles is concealed by the second chamber.

* * * * *